Figure 1A:
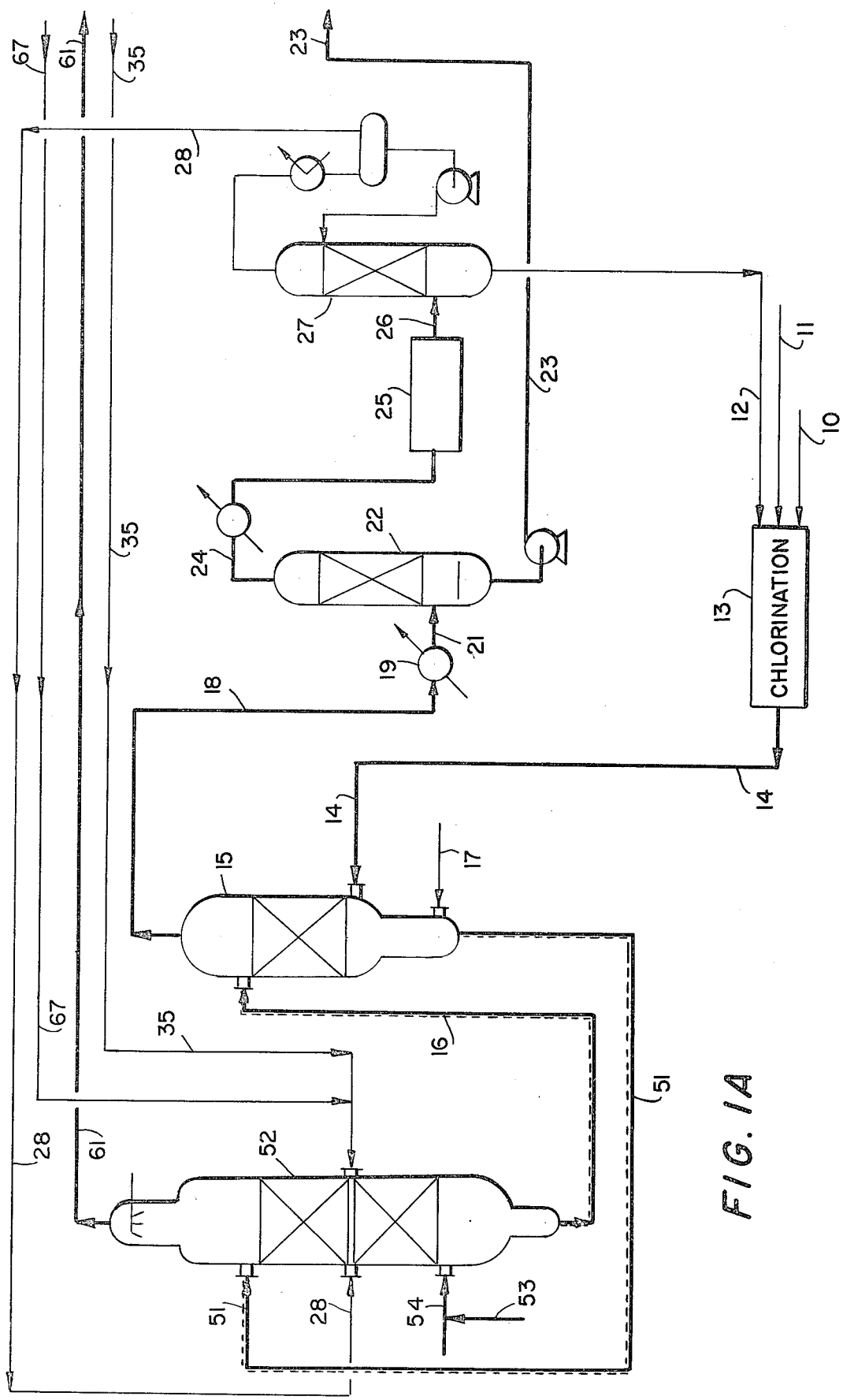
Figure 1B:
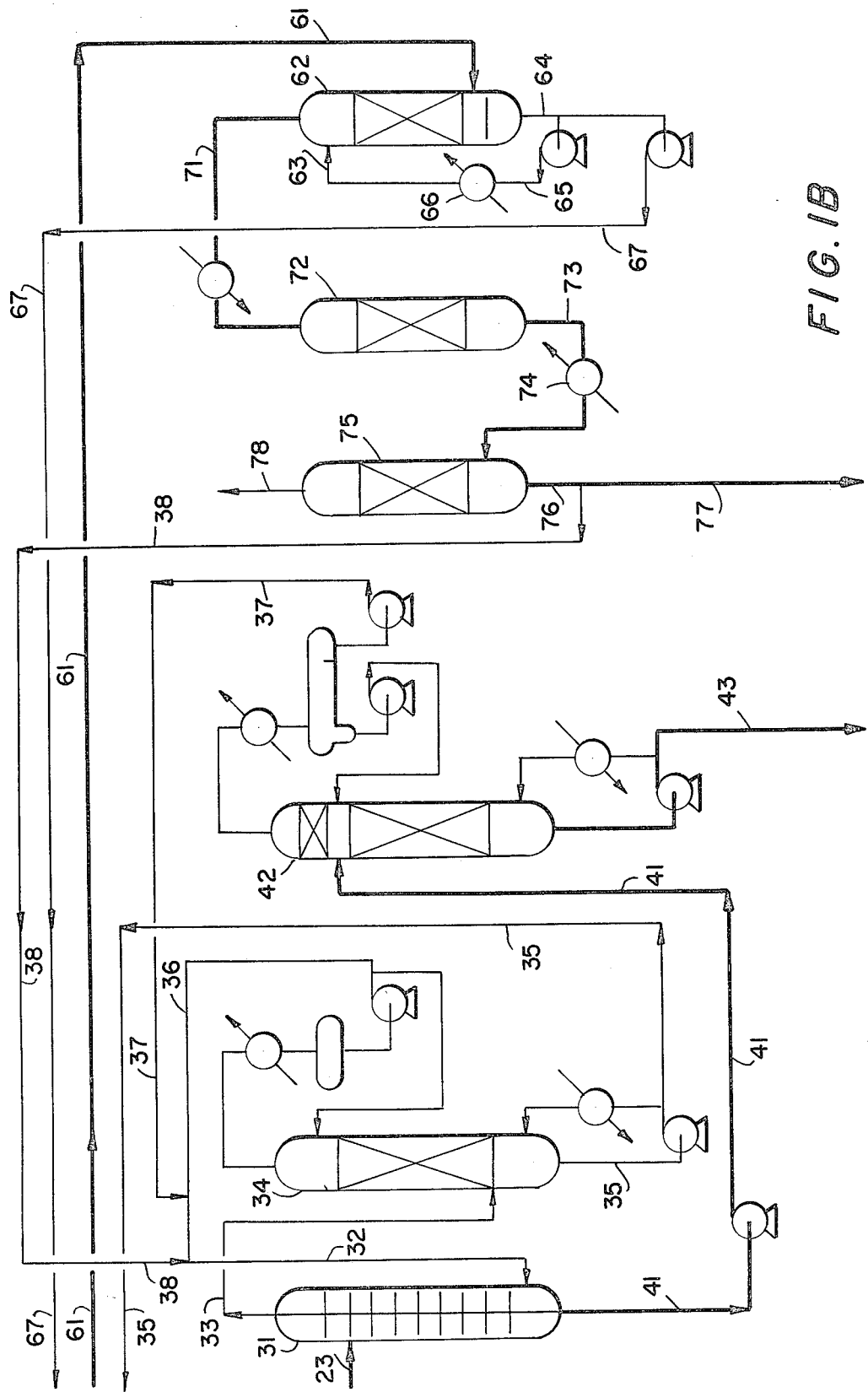

United States Patent [19]

Riegel

[11] 4,231,969
[45] Nov. 4, 1980

[54] PRODUCTION OF HEXACHLOROCYCLOPENTADIENE

[75] Inventor: Herbert Riegel, Maplewood, N.J.

[73] Assignee: The Lummus Company, Bloomfield, N.J.

[21] Appl. No.: 879,799

[22] Filed: Feb. 21, 1978

[51] Int. Cl.² .................................. C07C 23/08
[52] U.S. Cl. .......................... 570/223; 570/246; 570/214; 570/230
[58] Field of Search ........................ 260/648 C

[56] References Cited

U.S. PATENT DOCUMENTS 4,036,897  7/1977  Strangio et al. .............. 760/648 C Primary Examiner—C. Davis
Attorney, Agent, or Firm—Louis E. Marn; Elliot M. Olstein

[57] ABSTRACT

Hexachlorocyclopentadiene is produced by the use of a molten salt mixture of cuprous and cupric chloride, with the reaction effluent including the product, chlorine, hydrogen chloride, unreacted feed and organic byproduct, as well as entrained molten salt. The effluent is cooled at a temperature and pressure to effect condensation of organics, with the salt being present in the condensate. The salt is then separated from the organics for re-use in the process. Hydrogen chloride and chlorine present in the effluent are also recovered for re-use in the process.

20 Claims, 2 Drawing Figures

PRODUCTION OF HEXACHLOROCYCLOPENTADIENE

This invention relates to production of hexachlorocyclopentadiene.

Hexachlorocyclopentadiene (HCD) is used in the manufacture of pesticide, polymeric resins and plasticizers, and the demand for such a product has been steadily increasing. As a result, there is a need for new and improved processes for producing hexachlorocyclopentadiene.

In accordance with one embodiment of the present invention, a chlorinated $C_5$ saturated or mono-olefinically unsaturated hydrocarbon, which can be cyclic or acyclic, preferably a chlorinated $C_5$ saturated cyclic hydrocarbon, is contacted in a HCD production reactor with a salt mixture containing cuprous and cupric chloride, in molten form, to produce HCD. A gaseous effluent, containing HCD, chlorine, hydrogen chloride, unreacted feed and organic byproducts, which also contains entrained salt, is withdrawn from the HCD reactor, and is cooled to condense organics; namely, HCD and reaction byproducts and unreacted feed, with the condensate including the entrained salt. The entrained salt is separated from the condensate and passed to an oxidation reactor, along with salt withdrawn from the HCD production reactor, and in the oxidation reactor the salt is contacted with hydrogen chloride recovered from the gaseous effluent and molecular oxygen to enrich the salt in cupric chloride. The cupric chloride enriched salt is passed from the oxidation reactor to the HCD production reactor.

In accordance with an embodiment cyclopentadiene is employed as fresh feed for the ultimate production of hexachlorocyclopentadiene. In accordance with this embodiment, the cyclopentadiene is initially chlorinated to saturate the double bonds and produce chlorinated cyclopentane, which is then contacted in the HCD production zone, with a molten salt mixture of cuprous and cupric chloride to produce a reaction effluent containing hexachlorocyclopentadiene.

The chlorine present in the gaseous effluent from the HCD production reactor is recovered and recycled to the HCD production reactor and/or the initial chlorination reactor. In some cases, recovered chlorine which is to be introduced into the HCD production reactor is recycled to the initial chlorination reactor to provide for chlorination of fresh feed, with unreacted chlorine being then introduced into the HCD production reactor to meet the requirements thereof.

The molten salt contains a mixture of cuprous and cupric chloride, and generally also includes a metal chloride melting point depressant which is non-volatile and resistant to the action of oxygen at the process conditions in order to maintain the mixture of copper chloride in molten form. Suitable metal chloride melting point depressants are the alkali metal chlorides, such as potassium and lithium chloride, in particular, but it is to be understood that other metal chlorides and mixtures thereof such as the heavy metal chlorides; i.e., heavier than copper, of Groups I, II, III and IV of the Periodic Table; e.g., zinc, silver and thallium chloride, may also be employed. The metal chloride melting point depressant is added in an amount sufficient to maintain the salt mixture as a melt at the reaction temperatures, and is generally added in an amount sufficient to adjust the solidification point of the molten salt mixture to a temperature of below about 500° F. In using potassium chloride as a melting point depressant, the composition generally contains from about 20% to about 40%, by weight, of potassium chloride. The molten salt mixture may also contain other reaction promoters, such as rare earth metal chlorides.

In employing a saturated or mono-olefinically unsaturated $C_5$ hydrocarbon, or chloro substituted derivative thereof, as fresh feed, the $C_5$ hydrocarbon does not have any carbon atoms bonded directly to more than 2 carbon atoms, with the preferred starting materials being either pentene, isopentene, pentane, isopentane, cyclopentane, cyclopentene or the chlorinated derivatives thereof, with such chlorinated derivatives generally containing from 3 to 8 chlorine atoms.

In effecting the conversion of a starting material to hexachlorocyclopentadiene, the cupric chloride of the molten salt mixture provides chlorine values for the conversion. As should be apparent, the use of cupric chloride for providing chlorine values will result in a continuous depletion of the cupric chloride, and a net production of hydrogen chloride. Therefore, if the process is to be effected on a continuous basis, a provision must be made for regeneration of the cupric chloride and disposal of the hydrogen chloride. In the case where the starting material includes six chlorine atoms, the added chlorine values effect dehydrogenation and net production of hydrogen chloride.

In effecting the process on a continuous basis, the molten salt mixture of cupric and cuprous chloride is initially contacted in an oxidation reaction zone with an oxygen, containing gas and hydrogen chloride to enrich the cupric chloride content of the molten salt. The molten salt, now enriched in cupric chloride, is then employed for converting the hereinabove described feeds to hexachlorocyclopentadiene. The hydrogen chloride present in the reaction effluent may be recovered and recycled to the oxidation reaction zone to effect recovery thereof by reaction with oxygen and the molten salt to enrich the molten salt in cupric chloride. In this manner, hydrogen chloride present in the reaction effluent from the HCD production reactor is recovered for utilization in the production of HCD.

The production of the hexachlorocyclopentadiene by use of the molten mixture of cuprous and cupric chloride is generally effected at temperatures in the order of from about 750° F. to about 1000° F., preferably in the order of from about 800° F. to about 935° F. The reaction pressure may vary from about 1 to about 10 atm.

In accordance with a particularly preferred procedure of the present invention, it has been found that gaseous chlorine should be present during the production of the hexachlorocyclopentadiene in that such presence of chlorine reduces carbon formation. In general, the chlorine/$C_5$ hydrocarbon or chlorohydrocarbon feed ratio should range from 100% to 500% in excess of the stoichiometric ratio required to convert the $C_5$ hydrocarbon or chlorohydrocarbon feed to hexachlorocyclopentadiene product exclusive of the chlorine required for hydrogen removal. In such an embodiment, the reaction effluent from the hexachlorocyclopentadiene production zone will contain the excess chlorine plus any additional chlorine required in the effluent in gaseous form, and such gaseous chlorine is recovered from the effluent and recycled to the low temperature chlorination zone as required and to the HCD production reactor in order to maintain the hereinabove noted excess of gaseous chlorine. The temperature and pressure of the hexachlorocyclopentadiene production reactor and the cupric chloride content of the molten salt can be coordinated to insure that there is a sufficiently high chlorine vapor pressure over the molten salt in order to provide the desired excess of gaseous chlorine in such reactor and any additional chlorine required for the low temperature chlorination zone. Thus, for example, a sufficiently high chlorine vapor pressure to insure such excess can be maintained by controlling the cupric chloride content of the molten salt introduced into the reactor at a molar concentration of from 35 to 50%, preferably 40 to 45% with the cupric chloride to total copper mole ratio correspondingly being from about 0.50 to 0.70, preferably 0.55 to 0.65, and maintaining the reactor at a temperature of from 800° F. to 935° F. at a pressure of from 1 to 5 atm. The maintenance of a high chlorine vapor pressure over the salt is also enhanced by the inclusion of hydrogen chloride in the chlorine recycle stream.

In addition, in accordance with the preferred embodiment, the molten salt introduced into the hexachlorocyclopentadiene production reactor does not contain copper oxide. Thus, the oxidation reactor is operated in a manner such that the molten salt withdrawn therefrom does not contain copper oxide. Such a result is easily accomplished by introducing hydrogen chloride into the oxidation reactor in an amount sufficient to react with the added oxygen values to thereby enrich the salt in cupric chloride, and maintain the salt essentially free of copper oxide. It is to be understood that trace amounts may be present as an impurity.

In general, the oxidation reactor is operated at a temperature from about 750° F. to about 925° F. and at a pressure from about 1 to about 10 atm.

In accordance with the preferred aspect, the process is operated in a manner such that the circulating molten salt introduced into the top of the hexachlorocyclopentadiene production reactor has a temperature and a cupric chloride content which is higher than the circulating molten salt introduced into the top of the oxidation reactor, and that the hexachlorocyclopentadiene production reactor is operated at a pressure lower than the pressure of the oxidation reactor. In this manner, a high chlorine vapor pressure can be maintained at the top of the hexachlorocyclopentadiene production reactor to insure the desired presence of free chlorine in the HCD production reactor effluent, and a low chlorine vapor pressure can be maintained at the top of the oxidation reactor to increase the absorption of chlorine by the molten salt and minimize the presence of chlorine values in the gaseous effluent withdrawn from the oxidation reactor. The respective salt concentrations, temperatures and pressure are coordinated to provide for the desired chlorine value recovery in the oxidation reactor and the excess chlorine in the production reactor. In general, the salt introduced into the top of the hexachlorocyclopentadiene production reactor is at a temperature of from 20° F. to 175° F. greater than the temperature of the salt introduced into the oxidation reactor, with the production reactor being operated at a pressure of from 0 to 80 psi less than the oxidation reactor. Similarly, the cupric chloride content of the molten salt introduced into the hexachlorocyclopentadiene production reactor is from 1 mole % to 10 mole % greater than the cupric chloride content of the salt introduced into the oxidation reactor. The above conditions are only illustrative and the proper coordination of conditions is deemed to be within the scope of those skilled in the art from the teachings herein.

The molten salt mixture introduced into the hexachlorocyclopentadiene production reactor generally contains from about 35 mol % to about 50 mol %, and preferably from about 40 mol % to about 45 mol % of cupric chloride. As hereinabove noted, the molten salt is preferably free of copper oxide; however, if copper oxide is present in the molten salt introduced into the hexachlorocyclopentadiene production reactor, the amount of copper oxide can vary over a wide range and is generally controlled in a manner to provide a quantity thereof sufficient to react with the hydrogen chloride generated in the hexachlorocyclopentadiene production reactor. As representative examples of typical copper oxide contents, there may be mentioned amounts in the order of from 0.1 to 1.5 mole percent. Of course, lower amounts i.e., only a trace or essentially no copper oxide, or higher amounts could be employed depending upon the amount of conversion of liberated hydrogen chloride desired in the reactor, and the selection of appropriate amounts is deemed to be within the scope of those skilled in the art from the present teachings.

The reaction effluent may also contain chlorinated $C_5$ hydrocarbons which are potentially convertible to hexachlorocyclopentadiene, and such chlorinated $C_5$ hydrocarbons can be recovered and recycled to the hexachlorocyclopentadiene production reactor. In general, such chlorinated $C_5$ hydrocarbons are one or more of the following: $C_5Cl_8$; $C_5HCl_5$; and $C_{10}Cl_{10}$. Reaction intermediates such as octachlorocyclopentene are dechlorinated by contact with the molten salt to produce hexachlorocyclopentadiene.

In accordance with a preferred aspect, hexachlorocyclopentadiene is produced from cyclopentadiene, as starting material. In accordance with this aspect of the present invention, the cyclopentadiene is initially chlorinated at a relatively low temperature in order to effect saturation thereof. The chlorination of cyclopentadiene in order to effect saturation thereof is a reaction which is generally known in the art, and the particular conditions form no part of the present invention. In general, the chlorination is effected in the liquid phase at a temperature in the order of from about 0° C. to about 100° C., with the reaction preferably being effected at a temperature below about 60° C. The chlorination is effected in the presence or absence of a suitable diluent which is essentially inert in the reaction, with such diluent generally being a perchlorinated hydrocarbon The preferred inert diluent is liquid carbon tetrachloride; however, it is to be understood that other inert liquid diluents may also be employed for effecting such chlorination.

The initial chlorination is generally effected with an excess of chlorine in that in accordance with a preferred aspect, the chlorine values required for production of the final product are introduced into the initial chlorination stage. It is to be understood, however, that it is not necessary in all cases to operate with a chlorine excess.

The saturation of the cyclopentadiene with chlorine generally involves the addition of at least two moles of chlorine to saturate the two double bonds, with the chlorinated product containing generally at a minimum four chlorine atoms per mole of cyclopentadiene, with the product generally containing, at an average, of about 4 to 4.5 chlorine atoms per mole of cyclopentadiene. In accordance with one aspect of the present invention, the cyclopentadiene is saturated to provide six chlorine atoms per mole of cyclopentadiene.

Hydrogen chloride is also formed in the reaction, and a reaction product of chlorinated cyclopentadiene, containing at the mininum four chlorine atoms per mole of cyclopentadiene, and hydrogen chloride and excess chlorine, if any, is then introduced into the hexachlorocyclopentadiene production reactor for contact with the molten salt mixture of cuprous and cupric chloride to effect production of hexachlorocyclopentadiene. As hereinabove noted, in accordance with a preferred aspect, the molten salt is essentially free of copper oxide, and the reaction conditions are controlled to provide an excess of chlorine in the reactor in order to minimize carbon production.

The reaction effluent withdrawn from the hexachlorocyclopentadiene production reactor includes hexachlorocyclopentadiene reaction product, unreacted starting material, reaction intermediates, hydrogen chloride and chlorine, with such effluent being introduced into a separation and recovery zone. In the separation and recovery zone, hexachlorocyclopentadiene is recovered as product, with unreacted starting material and reaction intermediate being recovered and recycled to the hexachlorocyclopentadiene production reactor. In a preferred mode of operation the feed is fully converted single pass in the HCD reactor to hexachlorocyclopentadiene product plus reaction by-products.

The chlorine and hydrogen chloride present in the effluent may be recovered in admixture with each other, or as separate streams. The net hydrogen chloride, whether recovered separately or in admixture with chlorine, is introduced into an oxidation reactor along with molecular oxygen and molten salt recovered from the hexachlorocyclopentadiene production reactor wherein the hydrogen chloride and oxygen react with the molten salt to effect production of cupric chloride. The cupric chloride enriched salt is then recycled to the hexachlorocyclopentadiene production reactor.

The chlorine recovered from the reaction effluent is then recycled to the hexachlorocyclopentadiene production reactor in order to insure an excess of chlorine therein, and in the case where six atoms of chlorine are added in an initial chlorination stage, the chlorine recovered from the HCD production reaction effluent is recycled to the initial chlorination stage for ultimate introduction into the HCD production reactor.

In the case where hydrogen chloride and chlorine are recovered in admixture with each other, such a mixture is recycled to both the chlorination and the oxidation reactor, wherein the hydrogen chloride reacts with the oxygen and the molten salt, as hereinabove described, and wherein the chlorine reacts with cuprous chloride to also produce cupric chloride. The portion of the mixture of chlorine and hydrogen chloride recycled to the hexachlorocyclopentadiene production reactor insures an excess of chlorine therein to reduce carbon formation.

As should be apparent, the overall process involves reaction of chlorine and cyclopentadiene to produce as reaction product-hexachlorocyclopentadiene. The hydrogen chloride intermediate generated in the initial chlorination step and in the hexachlorocyclopentadiene production reactor is effectively recovered by reaction with the molten salt in the oxidation reactor to enrich the cupric chloride content of the molten salt, with such enriched molten salt then being employed to effect chlorination of the chlorinated cyclopentadiene reaction intermediate for ultimate production of hexachlorocyclopentadiene. Thus, by introducing chlorine and cyclopentadiene as fresh feed, the cyclopentadiene is ultimately converted to hexachlorocyclopentadiene.

In accordance with another embodiment, instead of using chlorine as fresh feed, the fresh feed is hydrogen chloride. In such an embodiment, hydrogen chloride, as fresh feed, is introduced into the oxidation reactor along with oxygen, wherein the hydrogen chloride and oxygen react with the molten salt to effect enrichment thereof in cupric chloride. The hydrogen chloride is introduced in an amount to provide the total chlorine values for converting cyclopentadiene to hexachlorocyclopentadiene; i.e., at least 6 atoms of chlorine per mole of cyclopentadiene fresh feed.

The molten salt enriched in cupric chloride is then introduced into the hexachlorocyclopentadiene production reactor along with the effluent from the reactor for chlorinating cyclopentadiene, which includes chlorinated cyclopentadiene and hydrogen chloride. In the reactor, the chlorinated cyclopentadiene intermediate is chlorinated by the cupric chloride of the molten salt to hexachlorocvclopentadiene, and in addition, chlorine values are stripped from the salt to provide net chlorine requirements for the initial chlorination of the cyclopentadiene.

The reaction effluent includes the hexachlorocyclopentadiene reaction product, unreacted starting material, reaction intermediates potentially convertible to the reaction product, hydrogen chloride produced in the initial chlorination reaction and in hexachlorocyclopentadiene production and chlorine, with such chloride requirements for the initial chlorination of cyclopentadiene; i.e., at least 4 chlorine atoms per mole of cyclopentadiene.

The net hydrogen chloride produced in the initial chlorination of cyclopentadiene and hexachlorocyclopentadiene production is recovered from the effluent and introduced into the oxidation reactor along with fresh feed hydrogen chloride wherein such chlorine values are recovered by enriching the cupric chloride content of the molten salt. The net chlorine present in the effluent is recovered and introduced into the initial chlorination reactor to effect chlorination of cyclopentadiene to the chlorinated cyclopentadiene reaction intermediate which is subsequently introduced into the hexachlorocyclopentadiene production reactor.

Thus, in accordance with this embodiment, hydrogen chloride provides the chlorine values for converting cyclopentadiene to hexacyclopentadiene, with the hydrogen chloride fresh feed being introduced into the oxidation reactor and the cyclopentadiene fresh feed being introduced into the initial chlorination reactor.

In accordance with the various embodiments of the present invention, the reaction effluent withdrawn from the hexachlorocyclopentadiene production zone may also contain chlorinated products which are not potentially and/or economically convertible to the desired product. Such reaction products may be burned in order to recover the chlorine values thereof as chlorine and/or hydrogen chloride, generally a mixture of chlorine and hydrogen chloride, and the combustion effluent can be introduced into the oxidation zone to recover such chlorine values by enriching the cupric chloride content of the molten salt.

In accordance with another aspect of the present invention, cyclopentadiene is contacted in an initial chlorination reactor with fresh feed chlorine and recycle chlorine to produce a chlorination effluent containing hexachlorocyclopentane, hydrogen chloride and preferably also chlorine. The chlorination effluent is introduced into the HCD production reactor, operated at conditions hereinabove described, wherein the effluent is contacted with a molten salt mixture containing cuprous and cupric chloride to dehydrogenate the hexachlorocyclopentane and strip chlorine from the salt to thereby produce an effluent containing hexachlorocyclopentadiene, hydrogen chloride and chlorine, and a molten salt mixture having a reduced content of cupric chloride.

Hexachlorocyclopentadiene, chlorine and hydrogen chloride are recovered from the gaseous effluent, with recovered chlorine being recycled to the initial chlorination reactor.

Recovered hydrogen chloride is introduced into the oxidation reactor, operated at conditions hereinabove described, and contacted with oxygen and molten salt from the HCD production reactor to recover hydrogen chloride by enriching the cupric chloride content of the molten salt. The molten salt enriched in cupric chloride is then recycled to the HCD production reactor.

The present invention will be further described with respect to embodiments thereof illustrated in the accompanying drawing, wherein:

The drawing is a simplified schematic flow diagram of an embodiment of the present invention.

Referring now to the drawing, fresh feed cyclopentadiene in line 10, fresh feed chlorine in line 11 and recycled chlorine, in line 12, obtained as hereinafter described, are introduced into an initial chlorination zone schematically generally indicated as 13. The initial chlorination zone 13 is operated at the conditions hereinabove described, and in particular, the chlorine is employed in an amount to effect addition of 6 atoms of chlorine to the cyclopentadiene feed; namely, to produce hexachlorocyclopentane.

A reaction effluent containing hexachlorocyclopentane, hydrogen chloride and excess chlorine is withdrawn from reaction zone 13 through line 14 and introduced into a hexachlorocyclopentadiene production reactor, schematically generally indicated as 15.

A molten salt, containing cuprous chloride, enriched in cupric chloride, and a melting point depressant, such as potassium chloride, is introduced into reactor 15 through line 16, with the salt being obtained as hereinafter described.

In reactor 15, the hexachlorocyclopentane feed is dehydrogenated to HCD, with the removed hydrogen combining with chlorine values generated from the cupric chloride present in the molten salt to produce hydrogen chloride. The HCD reaction zone 15 is operated at the conditions hereinabove described. In particular, reactor 15 is operated in the presence of an excess of chloride, as hereinabove described. The reactor is also operated in a manner to strip chlorine values from the molten salt for ultimate recovery and recycle to the initial chlorination reactor 13. For this purpose, a suitable stripping gas, such as hydrogen chloride, may be introduced into the bottom section of reactor 15 through line 17.

A gaseous reaction effluent, containing HCD, unreacted starting material, reaction byproducts, hydrogen chloride, chlorine and entrained salt is withdrawn from reactor 15 through line 18 and passed through a suitable cooler, generally indicated as 19, where the effluent is cooled to effect condensation of organics therefrom. The cooled effluent, in line 21, is introduced into a separator, schematically generally indicated as 22 to separate the condensed organics from the remaining gaseous effluent. The entrained salt is present in the condensed organic phase, with such condensed organic phase being withdrawn from separator 22 through line 23. The remaining gaseous effluent is withdrawn from separator 22 through line 24.

In general, the condensation of organics, including the entrained salt, is effected at a temperature in the order of from about 100° F. to about 200° F., preferably a temperature from about 100° F. to about 150° F., and at a pressure from about 1 to about 5 atm, and preferably from about 1 to about 2 atm.

The gaseous effluent in line 24 is passed through a compression and cooling zone, schematically generally indicated as 25 wherein the effluent is compressed and cooled in one or more stages to effect condensation of chlorine therefrom. In general, the effluent is cooled to a temperature in the order of from about 50° F. to about 100° F., preferably a temperature from about 50° F. to about 75° F., and is compressed to a pressure of from about 3 to about 20 atm, and preferably from about 6 to about 10 atm.

The cooled and compressed effluent in line 26 is introduced into a hydrogen chloride-chlorine separation column, schematically indicated as 27 to effect separation of a chlorine bottoms, from an overhead predominantly containing hydrogen chloride, and some amount of chlorine. In general, the column 27 is operated at an overhead temperature of from about $-70°$ F. to about $+20°$ F., a bottoms temperature from about 30° F. to about 150° F.

A chlorine bottoms is recovered from column 27 through line 12 and is recycled to the initial chlorination stage, as hereinabove described. The chlorine present in line 12 includes the excess chlorine to be maintained in the HCD production reactor 15 and chlorine values recovered from the hydrogen chloride generated in the initial chlorination stage 13.

The hydrogen chloride overhead recovered from column 27 through line 28, including some amounts of chlorine is recycled to the oxidation reactor, as hereinafter described, to effect recovery of such hydrogen chloride produced in the initial chlorination reactor 13, and hydrogen chloride generated in the HCD production reactor 15.

The organics, containing entrained salt, in line 23, is then introduced into a salt separation zone to effect recovery of the copper chloride salt from the organics. As particularly shown, the organics, containing entrained salt, in line 23, is introduced into a salt extraction column, schematically generally indicated as 31, wherein the organics are countercurrently contacted with aqueous hydrogen chloride, introduced through line 32 to extract the salt from the organic stream. In general, the extraction is effected at a temperature in the order of from about 100° F. to about 300° F., preferably from about 150° F. to about 200° F., with the hydrogen chloride, including the extracted salt being withdrawn from tower 31 through line 33.

The aqueous hydrogen chloride, containing copper chloride salts in line 33 is introduced into column 34 to effect separation of a bottoms stream containing salt dispersed in aqueous hydrogen chloride. The column 34 is operated at conditions to obtain a bottoms in which the salt is present in a concentration in the order of from about 1% to about 20%, preferably from about 5% to about 10%, all by weight. In addition, the column is operated in a manner to insure that the bottoms contains less than 20 ppm of organics, and preferably less than 10 ppm of organics. A bottoms of salt dispersed in aqueous hydrogen chloride is withdrawn from column 34 through line 35 for recycle to the oxidation reactor, as hereinafter described.

A gaseous overhead of hydrogen chloride, which contains any organics introduced into the column 34, is withdrawn through line 36, combined with hydrogen chloride from the organic purification, in line 37, obtained as hereinafter described, and further combined with makeup hydrogen chloride for the extraction, in line 38, obtained as hereinafter described, and the combined stream in line 32 introduced into column 31.

Organics separated in column 31, which are now free of salt, and which may contain minor amounts of aqueous hydrogen chloride, in line 41, is introduced into drying column, schematically generally indicated as 42, to effect drying of the organic product. The dried organic product is withdrawn from the column 42 through line 43 for further processing.

An overhead of aqueous hydrogen chloride which may contain some organics is recovered from column 42 through line 37 for ultimate recycle to the extraction column 31 as hereinabove described.

The crude organic product in line 43 is further processed to effect recovery of any recycle components, and to effect further recovery of final HCD product.

Referring back to the HCD production reactor 15, molten salt is withdrawn from the reactor 15 through line 51, and the molten salt is introduced into an oxidation reactor, schematically generally indicated as 52. The oxidation reactor 52 is provided with fresh feed oxygen, either as oxygen per se, or preferably in the form of air, through line 53 and is further provided with recycle hydrogen chloride values, obtained as hereinabove described in line 28 and line 35. The oxidation reactor 52 is further provided with chlorine and/or hydrogen chloride, generated by the conversion of waste chlorinated hydrocarbon byproducts, by procedures known in the art, with such chlorine values being provided through line 54. The oxidation reactor 52 is operated at the conditions hereinabove described to effect recovery of chlorine values by enriching the molten salt in its cupric chloride content. Thus, hydrogen chloride byproduct generated in the initial chlorination stage 13 and the HCD production reactor 15 is recovered in the oxidation reactor 52 by generating cupric chloride. Such chlorine values are ultimately recovered in reactor 15 by stripping chlorine from the salt. In addition, such chlorine values are re-utilized in reactor 15 for effecting dehydrogenation of the hexachlorocyclopentane feed to thereby produce HCD.

The molten salt, now enriched in cupric chloride, and preferably free of copper oxide, as hereinabove described, is withdrawn from oxidation reactor 52 through line 16 for introduction into the HCD production reactor 15.

A gaseous effluent, containing some hydrogen chloride, and chlorine, as well as water vapor, unreacted oxygen, carbon dioxide, nitrogen introduced with the air, is withdrawn from oxidation reactor 52 through line 61 and introduced into a direct contact quench vessel, schematically indicated as 62 wherein the effluent is directly contacted with an aqueous hydrogen chloride quench liquid, in line 63, to effect condensation of aqueous hydrogen chloride. Condensed aqueous hydrogen chloride is withdrawn from quench tower 62 through line 64, with a portion thereof being passed through line 65 including a quench cooler 66 for recycle to the tower 62 as quench liquid. Net aqueous hydrogen chloride is recovered through line 67 and may be combined with the recycle hydrogen chloride in line 35 for introduction into the oxidation reactor 52.

The remaining gaseous effluent is withdrawn from tower 62 through line 71 and introduced into a chlorine converter, schematically generally indicated as 72 wherein chlorine present in the effluent is converted to hydrogen chloride. The chlorine converter may be of a type known in the art, and no details in this respect are deemed necessary for a complete understanding of the present invention.

An effluent, containing hydrogen chloride, as well as water vapor, is withdrawn from chlorine converter 72 through line 73, cooled by cooler 74 to effect condensation of aqueous hydrogen chloride, and introduced into a separator, schematically generally indicated as 75. Condensed aqueous hydrogen chloride is withdrawn from separator 75 through line 76, and a portion thereof may be passed through line 38 to provide makeup hydrogen chloride requirements for the salt extraction. Net hydrogen chloride is recovered through line 77.

The remaining portion of the gaseous effluent is withdrawn from separator 75 through line 78 and such gaseous effluent may be further treated to effect neutralization of any remaining hydrogen chloride, and recovery of oxygen values, if economic, for recycle to the oxidation reactor.

Although the hereinabove described embodiment has been particularly described with reference to an overall process in which the initial chlorination is effected to produce hexachlorocyclopentane, it is to be understood that the overall embodiment could also be employed for the production of HCD wherein the initial chlorination is not effected in a manner such as to produce hexachlorocyclopentane.

In addition, although the embodiment has been particularly described with reference to recovering salt from the condensed organics by the use of an acid extraction, such salt can be recovered by other procedures. As a result, the hereinabove described invention is not limited to the particularly preferred embodiment.

Numerous modifications and variations of the present invention are possible in light of the above teachings, and therefore, within the scope of the appended claims, the invention may be practised otherwise than as particularly described.

I claim:
1. A process for producing hexachlorocylopentadiene, comprising:
  contacting in a hexachlorocyclopentadiene production zone a feed selected from the group consisting of chlorinated saturated $C_5$ hydrocarbons chlorinated mono-olefinically unsaturated $C_5$ hydrocarbons and mixtures thereof with a salt mixture containing cuprous chloride and cupric chloride, said salt mixture being in molten form;
  recovering a gaseous effluent containing hexachlorocyclopentadiene, other organics, chlorine, hydrogen chloride and entrained salt mixture;
  cooling the gaseous effluent to condense hexachlorocyclopentadiene and other organics and provide a condensate including said entrained salt mixture;
  separating said entrained salt mixture from the condensate;

introducing the separated entrained salt mixture into an oxidation reaction zone;

recovering chlorine and hydrogen chloride from the uncondensed gaseous effluent;

introducing recovered chlorine into the hexachlorocyclopentadiene production zone;

introducing recovered hydrogen chloride into the oxidation reaction zone;

contacting in the oxidation reaction zone molten salt mixture from the hexachlorocylopentadiene production zone and said separated entrained salt mixture with molecular oxygen, and said recovered hydrogen chloride to provide a molten salt enriched in cupric chloride; and passing said molten salt mixture enriched in cupric chloride to the hexachlorocyclopentadiene production zone.

2. The process of claim 1 wherein the chlorine and hydrogen chloride are recovered from the effluent in a separation column with the chlorine being recovered as liquid and the hydrogen chloride as gas.

3. The process of claim 2 wherein the hexachlorocyclopentadiene and other organics are condensed from the gaseous effluent at a temperature of from 100° F. to 200° F. and a pressure of from 1 to 5 atm.

4. The process of claim 1 wherein a gaseous effluent containing hydrogen chloride, chlorine and water vapor is withdrawn from said oxidation reaction zone, and further comprising recovering aqueous hydrogen chloride from the effluent from the oxidation reaction zone and recycling said recovered aqueous hydrogen chloride to the oxidation reaction zone; converting chlorine present in the effluent to hydrogen chloride and recovering hydrogen chloride produced from the chlorine as aqueous hydrogen chloride.

5. A process for producing hexachlorocyclopentadiene, comprising:
(a) contacting fresh feed chlorine and recovered chlorine with cyclopentadiene to produce an effluent containing chlorinated cyclopentane and hydrogen chloride;
(b) contacting in a hexachlorocyclopentadiene production zone effluent from step (a) with a salt mixture containing cuprous chloride and cupric chloride, said salt mixture being in molten form;
(c) recovering a gaseous effluent containing hexachlorocyclopentadiene other organics, chlorine, hydrogen chloride and entrained salt mixture;
(d) cooling the gaseous effluent to condense hexachlorocyclopentadiene and other organics and provide a condensate including said entrained salt mixture;
(e) separating said entrained salt mixture from the condensate;
(f) introducing separated entrained salt mixture into an oxidation reaction zone;
(g) recovering from the uncondensed effluent chlorine as a liquid stream and hydrogen chloride as a gaseous stream;
(h) passing recovered chlorine to step (a);
(i) introducing recovered hydrogen chloride into the oxidation reaction zone;
(j) contacting in the oxidation reaction zone molten salt mixture from the hexachlorocyclopentadiene production zone and said separated entrained salt mixture with molecular oxygen, and said recovered hydrogen chloride to provide a molten salt enriched in cupric chloride; and (k) passing said molten salt mixture enriched in cupric chloride to the hexachlorocyclopentadiene production zone.

6. The process of claim 5 wherein the hexachlorocyclopentadiene and other organics are condensed from the gaseous effluent at a temperature of from 100° F. to 200° F. and a pressure of from 1 to 5 atm.

7. A process for producing hexachlorocyclopentadiene, comprising:
(a) contacting fresh feed chlorine and recovered chlorine with cyclopentadiene to produce an effluent containing hexachlorocyclopentane and hydrogen chloride;
(b) contacting in a hexachlorocyclopentadiene production zone effluent from step (a) with a molten salt mixture containing cuprous chloride and cupric chloride to dehydrogenate said hexachlorocyclopentane and strip gaseous chlorine from the salt and thereby produce a gaseous effluent containing hexachlorocyclopentadiene, chlorine and hydrogen chloride;
(d) recovering chlorine, hydrogen chloride and hexachlorocyclopentadiene from the gaseous effluent;
(e) passing recovered chlorine to step (a);
(f) introducing the recovered hydrogen chloride into an oxidation reaction zone;
(g) contacting in the oxidation reaction zone molten salt mixture recovered from the hexachlorocyclopentadiene production zone with molecular oxygen, and recovered hydrogen chloride to provide a molten salt mixture enriched in cupric chloride; and
(k) recycling the molten salt mixture enriched in cupric chloride to the hexachlorocyclopentadiene production zone.

8. The process of claim 7 wherein the contacting of step (b) is effected at a temperature of from 750° F. to 1000° F.

9. The process of claim 8 wherein the molten salt mixture introduced into the hexachlorocyclopentadiene production zone is at a temperature of from 20° F. to 175° F. greater than the temperature of the molten salt mixture introduced into the oxidation reaction zone.

10. The process of claim 8 wherein the effluent from step (a) includes chlorine to maintain an excess of chlorine in the hexachlorocyclopentadiene production reaction zone.

11. A process for producing hexachlorocyclopentadiene, comprising:
contacting in a hexachlorocyclopentadiene production zone a feed selected from the group consisting of chlorinated saturated $C_5$ hydrocarbons chlorinated mono-olefinically unsaturated $C_5$ hydrocarbons and mixtures thereof with a salt mixture containing cuprous chloride and cupric chloride, said salt mixture being in molten form;
recovering a gaseous effluent containing hexachlorocyclopentadiene, other organics, chlorine, hydrogen chloride and entrained salt mixture;
cooling the gaseous effluent to condense hexachlorocyclopentadiene and other organics and provide a condensate including said entrained salt mixture;
separating said entrained salt mixture from the condensate by extraction, said extraction being effected with aqueous hydrogen chloride;

introducing the separated entrained salt mixture dispersed in the aqueous hydrogen chloride into an oxidation reaction zone;

recovering chlorine and hydrogen chloride from the uncondensed gaseous effluent;

introducing recovered chlorine into the hexachlorocyclopentadiene production zone;

introducing recovered hydrogen chloride into the oxidation reaction zone;

contacting in the oxidation reaction zone molten salt mixture from the hexachlorocyclopentadiene production zone and said separated entrained salt mixture with molecular oxygen, and said recovered hydrogen chloride to provide a molten salt enriched in cupric chloride; and passing said molten salt mixture enriched in cupric chloride to the hexachlorocyclopentadiene production zone.

12. The process of claim 11 wherein the dispersion of separated entrained salt mixture in aqueous hydrogen chloride is treated to reduce the organic content prior to introduction into the oxidation reaction zone.

13. The process of claim 11 wherein the feed is a chlorinated cyclopentane.

14. The process of claim 13 wherein the feed is hexachlorocyclopentane.

15. The process of claim 11 wherein an effluent which contains hydrogen chloride, chlorine and water vapor is withdrawn from the oxidation reaction zone, and aqueous hydrogen chloride recovered from the effluent from the oxidation reaction zone is employed for extraction of entrained salt mixture.

16. A process for producing hexachlorocyclopentadiene, comprising:
(a) contacting fresh feed chlorine and recovered chlorine with cyclopentadiene to produce an effluent containing chlorinated cyclopentane and hydrogen chloride;
(b) contacting in a hexachlorocyclopentadiene production zone effluent from step (a) with a salt mixture containing cuprous chloride and cupric chloride, said salt mixture being in molten form;
(c) recovering a gaseous effluent containing hexachlorocyclopentadiene, other organics, chlorine, hydrogen chloride and entrained salt mixture;
(d) cooling the gaseous effluent to condense hexachlorocyclopentadiene and other organics and provide a condensate including said entrained salt mixture;
(e) separating said entrained salt mixture from the condensate by extraction, said extraction being effected with aqueous hydrogen chloride;
(f) introducing separated entrained salt mixture dispersed in the aqueous hydrogen chloride, into an oxidation reaction zone;
(g) recovering from the uncodensed effluent chlorine as a liquid stream and hydrogen chloride as a gaseous stream;
(h) passing recovered chlorine to step (a);
(i) introducing recovered hydrogen chloride into the oxidation reaction zone;
(j) contacting in the oxidation reaction zone molten salt mixture from the hexachlorocyclopentadiene production zone and said separated entrained salt mixture with molecular oxygen, and said recovered hydrogen chloride to provide a molten salt enriched in cupric chloride; and
(k) passing said molten salt mixture enriched in cupric chloride to the hexachlorocyclopentadiene production zone.

17. The process of claim 16 wherein the feed is hexachlorocyclopentane.

18. The process of claim 16 wherein an effluent which contains hydrogen chloride, chlorine and water vapor is withdrawn from the oxidation reaction zone, and aqueous hydrogen chloride recovered from the effluent from the oxidation reaction zone is employed for extraction of entrained salt mixture.

19. A process for producing hexachlorocyclopentadiene, comprising:
(a) contacting fresh feed chlorine and recovered chlorine with cyclopentadiene to produce an effluent containing hexachlorocyclopentane and hydrogen chloride;
(b) contacting in a hexachlorocyclopentadiene production zone effluent from step (a) with a molten salt mixture containing cuprous chloride and cupric chloride to dehydrogenate said hexachlorocyclopentane and strip gaseous chlorine from the salt and thereby produce a gaseous effluent containing hexachlorocyclopentadiene, chlorine, hydrogen chloride, other organics and entrained salt mixture;
(c) cooling the gaseous effluent to condense hexachlorocyclopentadiene and other organics and provide a condensate including said entrained salt mixture;
(d) separating said entrained salt mixture from the condensate by extraction, said extraction being effected with aqueous hydrogen chloride;
(e) introducing the separated entrained salt mixture dispersed in the aqueous hydrogen chloride into an oxidation reaction zone;
(f) recovering chlorine and hydrogen chloride from the uncondensed gaseous effluent;
(g) passing recovered chlorine to step (a);
(h) introducing the recovered hydrogen chloride into the oxidation reaction zone;
(i) contacting in the oxidation reaction zone molten salt mixture recovered from the hexachlorocyclopentadiene production zone with molecular oxygen, and recovered hydrogen chloride to provide a molten salt mixture enriched in cupric chloride; and
(j) recycling the molten salt mixture enriched in cupric chloride to the hexachlorocyclopentadiene production zone.

20. The process of claim 19 wherein an effluent which contains hydrogen chloride, chlorine and water vapor is withdrawn from the oxidation reaction zone, and aqueous hydrogen chloride recovered from the effluent from the oxidation reaction zone is employed for extraction of entrained salt mixture.

* * * * *